United States Patent [19]
Lion et al.

[11] Patent Number: 5,989,570
[45] Date of Patent: Nov. 23, 1999

[54] COSMETIC AND DERMATOLOGICAL COMPOSITIONS CONTAINING A PLASTICIZING OLIGOMER AND A FILM-FORMING POLYMER AND USES THEREOF

[75] Inventors: Bertrand Lion, Livry Gargan; Christine Dupuis, Paris, both of France

[73] Assignee: L'Oreal, Paris, France

[21] Appl. No.: 08/885,809

[22] Filed: Jun. 30, 1997

[30] Foreign Application Priority Data

Jun. 28, 1996 [FR] France ..................................... 96 08114

[51] Int. Cl.⁶ ............................. A61K 7/48; A61K 7/025; A61K 7/04; A61K 7/06
[52] U.S. Cl. ............................. 424/401; 424/43; 424/47; 424/61; 424/64; 424/70.1; 424/70.7; 424/78.02; 424/78.03
[58] Field of Search .............................. 424/401, 61, 64, 424/70.7, 70.1, 78.02, 78.03, 43, 47

[56] References Cited

U.S. PATENT DOCUMENTS

| | | |
|---|---|---|
| 4,532,125 | 7/1985 | Vanlerberghe et al. . |
| 4,595,585 | 6/1986 | Papantoniou et al. . |
| 5,519,063 | 5/1996 | Mondet et al. ....................... 514/772.4 |
| 5,605,966 | 2/1997 | Schuler et al. . |
| 5,616,598 | 4/1997 | Lion et al. ............................... 514/374 |
| 5,660,820 | 8/1997 | Mondet et al. ....................... 424/70.16 |
| 5,807,540 | 9/1998 | Junino et al. . |

FOREIGN PATENT DOCUMENTS

| | | |
|---|---|---|
| 0602513 | 6/1994 | European Pat. Off. . |
| 2 239 480 | 2/1975 | France . |
| 2928190 | 1/1980 | Germany . |

OTHER PUBLICATIONS

JP 4–103513 Abstract (Apr. 1992).
JP 7–309728 Abstract (Nov. 1995).
JP 8–239308 Abstract (Sep. 1996).
Derwent Abstract of French Patent FR 2 239 480.

*Primary Examiner*—Jyothsna Venkat
*Attorney, Agent, or Firm*—Finnegan, Henderson, Farabow, Garrett & Dunner, L.L.P.

[57] ABSTRACT

A composition comprising at least one film forming polymer and at least one oligomer chosen from homopolymers or copolymers of monomers containing ethylenic unsaturation and polycondensates, having an average molecular weight, measured at the peak height by steric exclusion chromatography, ranging from 400 to 10,000 and having a glass transition temperature ranging from −80 to 10° C., the composition containing no film-forming polymer of the nitrocellulose type is disclosed.

Topical formulations formulated from this composition, in particular hair compositions for styling, holding and/or fixing the hair, and make-up compositions are also disclosed.

34 Claims, No Drawings

COSMETIC AND DERMATOLOGICAL COMPOSITIONS CONTAINING A PLASTICIZING OLIGOMER AND A FILM-FORMING POLYMER AND USES THEREOF

The present invention relates to the use of certain oligomers as plasticizers for a film-forming polymer in, and for the preparation of, cosmetic or dermatological compositions containing at least this film-forming polymer. The present invention also relates to topical formulations containing these plasticizers, in particular hair compositions for styling, holding and/or fixing the hair, and make-up and skin treatment compositions.

In cosmetic compositions based on film-forming polymers, in particular hair compositions for styling or holding the hair, such as aerosol lacquers, plasticizers are generally used in combination with film-forming polymers in order to lower the glass transition temperature of these polymers and to modify, according to the chosen application, the mechanical properties of the films resulting from the polymers, such as the flexibility. The plasticizers generally used are chosen from common non-volatile solvents for the film-forming polymer employed. These solvents remain trapped in the film-forming polymer deposit after drying. Certain plasticizing polymers of the ethylene glycol or propylene glycol polyether type are also known, such as the products Dowanol from the company Dow Chemical.

The Inventors have discovered, surprisingly, a novel family of plasticizers for the film-forming polymers usually used in cosmetics, including specific oligomers which will be defined in detail later. These oligomers lead to better efficacy in the plasticization of the film-forming polymers than the standard plasticizers.

When they are used in styling products based on film-forming polymers, such as hair-fixing lacquers, the oligomers in accordance with the invention make it possible in particular to obtain, with smaller amounts, a lacquering power which is equivalent to that obtained with standard plasticizers using larger amounts, while at the same time significantly improving the cosmetic properties of the hair, such as its disentangling and its feel after the product has been applied.

When they are used in make-up products for the eyelashes or the eyebrows, such as mascaras or eyeliners, the oligomers in accordance with the invention also make it possible, by virtue of their noteworthy properties of plasticizing the film-forming polymers generally used in this application, to promote the spreading of the deposit and to obtain good flexibility of the deposit with lower amounts than those generally used with standard plasticizers.

When they are used in make-up products for the nails, such as nail varnishes, the oligomers in accordance with the invention also make it possible, by virtue of their noteworthy properties of plasticizing the film-forming polymers generally used in this application, to improve the sheen with lower amounts than those generally used with standard plasticizers. In addition, in contrast with standard plasticizers, they do not lead to any phenomena of surface migration or to phenomena of loss by evaporation over time.

A main subject of the invention includes the use of at least one specific oligomer which will be defined later as a plasticizer for a film-forming polymer in, and for the preparation of, cosmetic or dermatological compositions containing at least this film-forming polymer, these compositions containing no film-forming polymer of the nitrocellulose type.

Another subject of the invention includes cosmetic or dermatological compositions containing at least one film-forming polymer and at least one plasticizer for the polymer which is chosen from the specific oligomers which will be defined later.

Other subjects will become apparent on reading the description and the examples which follow.

The expression plasticizer for a given film-forming polymer is understood to refer to any substance which is compatible with the polymer and is capable of combining with or inserting into the polymer such that the mixture obtained has a glass transition temperature and a softening point which are below those of the film-forming polymer alone, and thus gives the polymer greater flexibility.

The oligomers of the invention are chosen from homopolymers or copolymers of monomer(s) containing ethylenic unsaturation and polycondensates, having an average molecular weight, measured at the peak height by steric exclusion chromatography, ranging from 400 to 10,000, and having a glass transition temperature ranging from –80 to 10° C. Their average molecular weight, measured at the peak height by steric exclusion chromatography, ranges more particularly from 500 to 5000. Their glass transition temperature ranges more particularly from –70 to 5° C.

The oligomers according to the invention containing a polymer of at least one monomer containing ethylenic unsaturation are chosen, for example, from acrylic, methacrylic, allylic, methallylic or vinyl homopolymers or copolymers. They may be anionic, cationic, amphoteric or nonionic.

These monomers containing ethylenic unsaturation may be chosen in particular from:

acrylic or methacrylic esters or amides obtained from linear, branched or cyclic aliphatic alcohols and/or from aromatic alcohols, which are preferably $C_1$–$C_{30}$, such as methyl (meth)acrylate, ethyl (meth)acrylate, propyl (meth)acrylate, butyl (meth)acrylate, isobutyl (meth)acrylate, tert-butyl (meth)acrylate and tert-butylacrylamide;

vinyl, allylic or methallylic esters or amides obtained from linear, branched or cyclic aliphatic alcohols and/or from aromatic alcohols, which are preferably $C_1$–$C_{30}$, such as vinyl acetate, vinyl propionate, vinyl benzoate and vinyl tert-butylbenzoate;

olefins such as ethylene, propylene, styrene and substituted styrene;

halo or perhalo and more particularly fluoro or perfluoro acrylic and vinyl monomers; or mixtures thereof.

Among the anionic monomers containing ethylenic unsaturation, mention may be made of:

monomers containing at least one acid function, in free form or in partially or totally neutralized form, such as monocarboxylic acids, for instance acrylic acid, methacrylic acid or crotonic acid; dicarboxylic acids or acid anhydrides as well as the monoesters or monoamides thereof, for instance maleic anhydride in diacid, monoester or monoamide form, and itaconic acid;

monomers containing at least one sulphonic acid function, in free form or in partially or totally neutralized form, such as vinylsulphonic or styrenesulphonic acid or 2-acrylamido-2-methylpropanesulphonic acid;

monomers containing at least one phosphoric or phosphonic acid function, in free form or in partially or totally neutralized form.

These anionic monomers are preferably partially or totally neutralized with a monobasic compound such as an inorganic base, for example sodium hydroxide or potassium hydroxide, or an amino alcohol taken, for example, from the group including 2-amino-2-methyl-1-propanol (AMP), triethanolamine, triisopropanolamine (TIPA), monoethanolamine, tri[(2-hydroxy)-1-propyl amine, 2-amino-2-methyl-1,3-propanediol (AMPD) and 2-amino-2-hydroxymethyl-1,3-propanediol.

Among the cationic monomers containing ethylenic unsaturation, mention may be made of:

monomers containing an amine function in free form or partially or totally neutralized or alternatively partially or totally quaternized, such as dimethylaminoethyl (meth)acrylate, dimethylaminoethylmethacrylamide, vinylamine, vinylpyridine and diallyldimethylammonium chloride.

These cationic monomers are preferably partially or totally neutralized with an inorganic or organic acid such as hydrochloric acid, acetic acid, lactic acid or glycolic acid or are partially or totally quaternized with an alkyl, cycloalkyl or aryl halide or a dialkyl (dimethyl or diethyl) sulphate.

Among the amphoteric monomers containing ethylenic unsaturation, mention may be made of:

carboxybetaines or sulphobetaines obtained by partial or total quaternization of monomers containing ethylenic unsaturation and containing an amine function, with sodium salts of a carboxylic acid containing a labile halide (sodium chloroacetate) or with cyclic sultones (propanesultone).

Among the nonionic monomers containing ethylenic unsaturation, mention may be made of:

hydroxy($C_1$–$C_{30}$)alkyl (meth)acrylates such as 2-hydroxyethyl (meth)acrylate and 2-hydroxypropyl (meth)acrylate;

acrylamides such as acrylamide, methacrylamide and di($C_1$–$C_{30}$)alkyl (meth)acrylamides;

N-vinylpyrrolidone, vinylcaprolactam;

(meth)acrylates of ethylene glycol, of diethylene glycol or of polyethylene glycol containing a hydroxyl or ether end.

The oligomers including a polymer of at least one monomer containing ethylenic unsaturation may be obtained by standard radical polymerization processes adapted for the production of low molecular weights. Solution, suspension, emulsion, precipitation or dispersion polymerization methods may be mentioned. To promote the production of low molecular weights, large amounts of transfer agents are preferably used in order to adjust the molecular weight more easily. In this respect, mention can be made of teleomerization processes as defined in the encyclopedia "Comprehensive Polymer Science", Vol. 3, pages 185–194, Pergamon Press, 1989, the disclosure of which is incorporated herein by reference.

The oligomers of the polycondensate type according to the invention are chosen, for example, from polyesters, polyester/amides, polyamides, polyurethanes and polyureas or mixtures thereof. They may be anionic, cationic, amphoteric or nonionic.

The polyesters, the polyester/amides and the polyamides may result, for example, from polycondensation between diols, dicarboxylic acids, amino alcohols or diamines which may contain fatty side chains that are preferably saturated. They may also result from the self-polycondensation of a compound containing both a reactive carboxylic acid group and a reactive alcohol group or alternatively containing both a reactive carboxylic acid group and a reactive amine group. Among the monomers present in the polycondensation medium, mention can also be made of the possible presence of carboxylic anhydrides (phthalic anhydride) and of compounds containing only one reactive group, such as monoalcohols, monoamines and monocarboxylic acids, which are preferably fatty. The mono- or difunctional polycondensation monomers are of linear, branched or cyclic aliphatic nature or alternatively of aromatic nature.

The polyesters, the polyester/amides and the polyamides are obtained according to standard methods of polycondensation in the molten state, in solution or in dispersion.

A particularly preferred family of oligomers in accordance with the invention includes polyesters which may be obtained by polycondensation of at least one dicarboxylic acid chosen from the group:

(i) the compounds of formula (I) below:

$$HOOC-(CH_2)_m-COOH \qquad (I)$$

where m is an integer ranging from 2 to 20;

(ii) the compounds of formula (II) below:

the labile acid group preferably being in the ortho, para or meta position and it being possible for the benzene ring to contain substituents other than sulphonate groups;

(iii) mixtures thereof, with a diol chosen from the group including of:

(a) the compounds of formula (III) below:

$$HO-(CH_2)_x-OH \qquad (III)$$

where x is an integer ranging from 2 to 20;

(b) the compounds of formula (IV) below:

where P is an aromatic, cycloaliphatic or linear or branched aliphatic trivalent hydrocarbon radical, preferably a group —$(CH_2)_p$—CH— with $p \geq 1$, and more particularly the —$CH_2$—CH— group and $R_1$ denotes a $C_2$–$C_{30}$ hydrocarbon side chain;

(c) the compounds of formula (V) below:

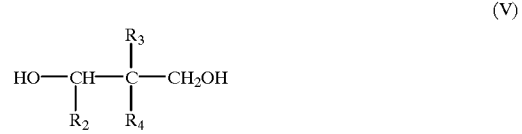

where $R_2$ denotes a hydrogen atom or a linear or branched $C_1$–$C_3$ alkyl radical; $R_3$ denotes a hydrogen atom or a linear or branched $C_1$–$C_4$ alkyl radical and $R_4$ denotes a linear or branched $C_1$–$C_4$ alkyl radical;

(d) the compound of formula (VI) below:

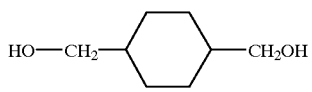

(VI)

(e) the compound of formula (VII) below:

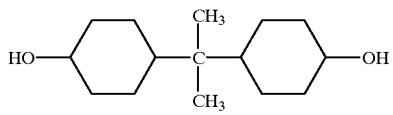

(VII)

(f) mixtures thereof.

The cosmetic and dermatological compositions according to the invention therefore contain, in a cosmetically or dermatologically acceptable vehicle, at least one film-forming polymer and at least one oligomer or telomer as defined above, as a plasticizer for the film-forming polymer, for applications as varied as those encountered, for example, in the field of hair, of make-up or of skincare, or any other cosmetic field in which the use of a film-forming substance is desirable or sought.

Among the applications preferably targeted by the present invention, mention may be made more particularly of:

the field of hair products (hair washing, hair care or hair beauty) in which the compositions according to the invention may be in the form of aerosols, foam, shampoos, conditioners, styling or treating lotions or gels, hair shaping, hair setting or fixing lacquers or lotions.

the field of make-up products, in particular for making up the nails, the eyelashes or the lips, in which the compositions according to the invention may be in the form of nail varnish; mascaras or eye-liners; or lipsticks.

in the field of skincare products, e.g., creams, milks, lotions, masks, sera, or antisun products.

The plasticizers in accordance with the invention are preferably used in solids concentrations ranging from 0.1 to 80% by weight, more preferably from 5 to 40%, and still more preferably from 10 to 30% by weight, relative to the total weight of the composition.

The film-forming polymers to be plasticized which are used in the compositions of the invention are those which are usually used for the various applications mentioned above. They are chosen, for example, from the polymers described above in the present application, as well as from those described in French applications FR 2,439,798 and FR 2,697,160 and French patent FR 92/13600.

Mention may be made in particular of:

the vinyl acetate/crotonic acid/vinyl tert-butylbenzoate copolymers described in French Patent No. 2,439,798;

acrylic acid/ethyl acrylate/N-tert-butylacrylamide copolymers, such as the product sold under the name Ultrahold Strong by the company BASF;

N-octylacrylamide/methyl methacrylate/hydroxypropyl methacrylate/acrylic acid/tert-butylaminoethyl methacrylate copolymers such as the product sold under the name Amphomer LV 71 by the company National Starch; and acrylic acid/ethyl acrylate/tert-butyl acrylate terpolymers such as the product sold under the name Luvimer 100P by the company BASF.

The concentration of film-forming polymer in the cosmetic or dermatological compositions of the invention generally ranges from 0.1 to 50%, and preferably from 1 to 30%, by weight relative to the total weight of the composition. It varies according to the cosmetic or dermatological application envisaged.

The cosmetically acceptable vehicle for the compositions according to the invention preferably includes water, one or more cosmetically acceptable organic solvents, or alternatively, a mixture of water and one or more cosmetically acceptable organic solvents.

Among these organic solvents, $C_1$–$C_4$ lower alcohols such as ethanol are used more particularly, especially in the hair products. For nail varnishes or nail care bases, mixtures of butyl acetate and ethyl acetate are used more particularly.

The vehicle may also include fatty substances such as mineral oils, plant oils, animal oils or synthetic oils, animal waxes, fossil waxes, plant waxes, mineral waxes or synthetic waxes.

The film-forming polymers according to the invention are dissolved or dispersed in the vehicle for the compositions of the invention.

The plasticizers in accordance with the invention are dissolved or dispersed in the vehicle for the compositions of the invention.

The compositions may also, of course, contain various adjuvants intended to make it acceptable in a particular cosmetic application.

The compositions according to the invention may also contain conventional cosmetic additives chosen from fatty substances such as mineral oils, plant oils, animal oils or synthetic oils, animal waxes, fossil waxes, plant waxes, mineral waxes or synthetic waxes, organic solvents, thickeners, softeners, antifoaming agents, hydrating agents, wetting agents, treating agents (agents for combatting hair loss, antidandruff agents, etc.), antiperspirants, basifying agents, UV-A or UV-B or broad-band sunscreens, dyes, pigments, fragrances, preserving agents, anionic, nonionic or amphoteric organic polymers which are compatible with the grafted copolymers of the invention, and propellants when the compositions are in aerosol form.

Obviously, a person skilled in the art will take care to select the optional complementary compound or compounds mentioned above such that the advantageous properties intrinsically associated with the compositions according to the invention are not, or are not substantially, adversely affected by the addition or additions envisaged.

Another subject of the invention is a process for the cosmetic treatment of keratin substances such as the skin, the hair, the scalp, the eyelashes, the eyebrows, the nails or the lips, characterized in that it comprises applying a composition as defined above to these keratin substances.

The examples which follow serve to illustrate the invention without, however, being limiting in nature.

PREPARATION EXAMPLES

Preparation Example 1

Synthesis of a Polyneopentyl Glycol Sebacate Polyester with an Average Molecular Weight of 600 and Containing α, ω-hydroxyl ends Composition of the starting materials:

| | |
|---|---|
| Dimethyl sebacate | 276 g (1.2 M) |
| 2,2-dimethyl-1,3-propanediol (also | 274.6 g (2.64 M) |

-continued

| | |
|---|---|
| known as neopentyl glycol) | |
| Zinc acetate dihydrate in a weight/ charge proportion of 0.3% | 1.6 g |
| Pure 1,2-dichloroethane | 2 l |
| Deionized water | 2 l |

PROCEDURE

A 500 ml cylindrical reactor fitted with a nitrogen inlet, a thermometer and a distillation assembly was used. The reactor was heated with a Wood's alloy bath.

The premolten dimethyl sebacate (melting point 25–28° C.) and 2,2-dimethyl-1,3-propanediol (melting point 126–128° C.) were introduced into the reactor. The mixture was heated from room temperature to 150° C. over 1 hour. The reaction mixture became clear at about 100° C. As soon as the reaction mixture reached 150° C., zinc acetate was introduced. The synthesis was left to proceed for 3 hours at 150° C., while collecting the methanol formed. The temperature was then increased to 200° C. over 45 minutes and was then maintained for 3 hours at 200° C. The methanol distillation continued throughout the condensation.

After 3 hours at 200° C., the mixture was cooled to room temperature while reducing the stirring. As soon as the internal temperature reached 50° C., 300 ml of 1,2-dichloroethane were added.

The synthesis solution was recovered and diluted with 1.7 l of 1,2-dichloroethane. The excess 2,2-dimethyl-1,3-propanediol was then extracted twice with 1 liter of deionized water. During these two extractions, an interface emulsion may have formed. This emulsion, if formed, was readily eliminated by heating the water used during the extraction. The organic phase was recovered and dried over anhydrous sodium sulphate. The dried solution was filtered and the 1,2-dichloroethane was evaporated off until the dry product was recovered.

This polymer was in the form of a viscous liquid at room temperature.

CHARACTERIZATION:

| | |
|---|---|
| Hydroxyl number: | 190–195 |
| Molecular weight measured: at the peak height by steric exclusion chromatography | 600 |

Preparation Example 2

Synthesis of a Neopentyl Glycol Sebacate/terephthalate Copolymer with an Average Molecular Weight of 600–700 and Containing α, ω-hydroxyl ends Composition of the starting materials:

| | |
|---|---|
| Dimethyl terephthalate | 116.4 g (0.6 M) |
| Dimethyl sebacate | 138 g (0.6 M) |
| 2,2-Dimethyl-1,3-propanediol (also known as neopentyl glycol) | 274.6 g (2.64 M) |
| Zinc acetate dihydrate in a weight/ reactant proportion of 0.3% | 1.6 g |
| Pure 1,2-dichloroethane | 2 l |
| Deionized water | 2 l |

PROCEDURE

A 500 ml cylindrical reactor fitted with a nitrogen inlet, a thermometer and a distillation assembly was used. The reactor was heated with a Wood's alloy bath.

The premolten dimethyl sebacate (melting point 25–28° C.) and 2,2-dimethyl-1,3-propanediol (melting point 126–128° C.) were introduced into the reactor. The mixture was heated from room temperature to 150° C. over 1 hour. As soon as the reaction medium became clear, at about 100° C., the dimethyl terephthalate was added. As soon as the reaction mixture reached 150° C., zinc acetate was introduced. The synthesis was left to proceed for 3 hours at 150° C., while collecting the methanol formed. The temperature was then increased to 200° C. over 45 minutes and was then maintained for 3 hours at 200° C. The methanol distillation continued throughout the condensation.

After 3 hours at 200° C., the mixture was cooled to room temperature while reducing the stirring. As soon as the internal temperature reached 50° C., 300 ml of 1,2-dichloroethane were added.

The synthesis solution was recovered and diluted with 1.7 l of 1,2-dichloroethane. The excess 2,2-dimethyl-1,3-propanediol was then extracted twice with 1 liter of deionized water. During these two extractions, an interface emulsion may have formed. This emulsion, if formed, was readily eliminated by heating the water used during the extraction. The organic phase was recovered and dried over anhydrous sodium sulphate. The dried solution was filtered and the 1,2-dichloroethane was evaporated off until the dry product was recovered.

The polymer was in the form of a paste at room temperature and became liquid at 50° C.

CHARACTERIZATION:

| | |
|---|---|
| Hydroxyl number: | 189–192 |
| Molecular weight measured: at the peak height by steric exclusion chromatography | 600 |

APPLICATION EXAMPLES

Example 3

Aerosol Lacquer

Lacquer composition:

| | |
|---|---|
| Vinyl acetate/vinyl tert-butylbenzoate/ crotonic acid copolymer (65/25/10% by weight) with a molecular weight of 100,000, described in patent FR 2,439,798 (film-forming polymer) | 8.6 g |
| 2-Amino-2-methylpropanol (neutralizing agent) | 0.86 g |
| Polyester oligomer of Example 1 (plasticizer) | 0.43 g |
| Absolute ethanol | qs 100 g |

Pressurization:

| | |
|---|---|
| Lacquer composition | 37 g |
| Dimethyl ether | 43 g |
| Pentane | 20 g |

When compared with a formulation containing a standard plasticizer of the polyglycol ether type in the same amount, this formulation, sprayed onto the hair, led to easier disentangling, greater softness and a markedly more pleasant, smoother and lighter feel, and with no charge effect, for an equivalent level of fixing.

Example 4

Aerosol Lacquer

Lacquer composition:

| | |
|---|---|
| Acrylic acid/ethyl acrylate/N-tert-butyl acrylamide copolymer sold under the name Ultrahold Strong by BASF | 12 g |
| 2-Amino-2-methylpropanol (neutralizing agent) | 1.5 g |
| Polyester oligomer of Example 1 (plasticizer) | 0.6 g |
| Water | 33.5 g |
| Absolute ethanol | qs 100 g |

Pressurization:

| | |
|---|---|
| Lacquer composition | 45% |
| Dimethyl ether | 55% |

When compared with a formulation containing a standard plasticizer of the polyglycol ether type in the same amount, this formulation, sprayed onto the hair, led to easier disentangling, greater softness and a markedly more pleasant, smoother and lighter feel, and with no charge effect, for an equivalent level of fixing.

Example 5

Aerosol Lacquer

Lacquer composition:

| | |
|---|---|
| Vinyl acetate/vinyl tert-butylbenzoate/crotonic acid copolymer (65/25/10% by weight) with a molecular weight of [lacuna], described in patent FR 2,439,798 (film-forming polymer) | 5.3 g |
| 2-Amino-2-methylpropanol (neutralizing agent) | 0.54 g |
| Polyester oligomer of Example 2 (plasticizer) | 0.16 g |
| Absolute ethanol | 30.8 g |
| Water | qs 100 g |

Pressurization:

| | |
|---|---|
| Lacquer composition | 65% |
| Dimethyl ether | 35% |

This formulation led to good hair-fixing properties and gave hair which felt smooth and clean and less dry than with standard formulations based on common plasticizers.

Example 6

Spray in a Pump-Dispenser Bottle

| | |
|---|---|
| Acrylic acid/ethyl acrylate/tert-butyl acrylate terpolymer solid under the name Luvimer 100P by the company BASF (film-forming polymer) | 7.0 g |
| 2-Amino-2-methylpropanol (neutralizing agent) | qs 100% neutralization |
| Polyester oligomer of Example 2 (plasticizer) | 0.35 g |
| Absolute ethanol | qs 100 g |

This formulation led to good hair-fixing properties and gave hair which felt smooth and clean and less dry than with standard formulations based on common plasticizers.

Example 7

Aerosol Lacquer

Lacquer composition:

| | |
|---|---|
| N-octylacrylamide/methyl methacrylate/hydroxypropyl methacrylate/acrylic acid/tert-butylaminoethyl methacrylate copolymer sold under the name Amphomer LV71 by National Starch (film-forming polymer) | 15 g |
| 2-Amino-2-methylpropanol (neutralizing agent) | qs 100% neutralization |
| Polyester oligomer of Example 1 (plasticizer) | 0.7 g |
| Water | 33.5 g |
| Absolute ethanol | qs 100 g |

Pressurization:

| | |
|---|---|
| Lacquer composition | 45% |
| Dimethyl ether | 55% |

This formulation led to good hair-fixing properties and gave hair which felt smooth and clean and less dry than with standard formulations based on common plasticizers.

Example 8

Nail Varnish

| | |
|---|---|
| Chlorinated grafted copolymer described in Example 1 of patent FR 92/13600 (film-forming polymer) | 23% |
| Heptane | 10% |
| Ethyl acetate | 20% |
| Butyl acetate | 34.9% |
| Polyester oligomer of Example 1 (plasticizer) | 10% |
| Pigments | 0.8% |
| Thixotropic agent | 1.2% |
| Citric acid | 0.1% |

The varnish obtained was shiny and had good staying power.

Example 9

Nail Varnish

| | |
|---|---|
| Chlorinated grafted copolymer described in Example 1 of patent FR 92/13600 (film-forming polymer) | 23% |
| Heptane | 10% |
| Ethyl acetate | 20% |
| Butyl acetate | 34.9% |
| Polyester oligomer of Example 2 (plasticizer) | 10% |
| Pigments | 0.8% |
| Thixotropic agent | 1.2% |
| Citric acid | 0.1% |

The varnish obtained was shiny and had good staying power.

What is claimed is:

1. A cosmetic or dermatological composition, said composition comprising at least one film forming polymer and at least one oligomer for plasticizing said at least one film-forming polymer, said at least one plasticizing oligomer being a homopolymer or copolymer of at least one monomer containing ethylenic unsaturation or a polycondensate, said at least one plasticizing oligomer having an average molecular weight, measured at the peak height by stearic exclusion chromatography, ranging from 400 to 10,000 and having a glass transition temperature ranging from −80° to 10° C., wherein said composition is free of nitrocellulose film-forming polymers.

2. The composition according to claim 1, wherein said plasticizing oligomer has an average molecular weight, measured at the peak height by steric exclusion chromatography, ranging from 500 to 5,000.

3. The composition according to claim 1, wherein said plasticizing oligomer has a glass transition temperature ranging from −70 to 5° C.

4. The composition according to claim 1, wherein said plasticizing oligomer is:
   an anionic, cationic, amphoteric or nonionic acrylic, methacrylic, allylic, methallylic or vinyl homopolymer; or
   an anionic, cationic, amphoteric or nonionic acrylic, methacrylic, allylic, methallylic or vinyl copolymer.

5. The composition according to claim 1, wherein said plasticizing oligomer is a polymer of at least one monomer, said monomer is:
   an acrylic or a methacrylic ester or amide obtained from a linear, branched or cyclic aliphatic alcohol, from an aromatic alcohol or from a mixture of both an aliphatic and an aromatic alcohol;
   a vinyl, an allylic or a methallylic ester or amide obtained from a linear, branched or cyclic aliphatic alcohol, from an aromatic alcohol or from a mixture of both an aliphatic and an aromatic alcohol,
   an olefin;
   a halo or perhalo acrylic or vinyl monomer; or
   a mixture of any of the above.

6. The composition according to claim 5, wherein said cyclic aliphatic alcohol, said aromatic alcohol or mixtures of said aliphatic alcohol and said aromatic alcohol have from 1 to 30 carbon atoms.

7. The composition according to claim 5, wherein said halo or perhalo acrylic or vinyl monomers are fluoro or perfluoro acrylic or vinyl monomers.

8. The composition according to claim 1, wherein said plasticizing oligomer is a polymer of at least one monomer, said monomer is:
   a monomer having at least one acid function, said at least one acid function being in free form or in partially or totally neutralized form;
   a monomer having at least one sulphonic acid function, said at least one sulphonic acid function being in free form or in partially or totally neutralized form; or
   a monomer having at least one phosphoric or phosphoric acid function, said at least one phosphoric or phosphoric acid function being in free form or in partially or totally neutralized form.

9. The composition according to claim 8, wherein said monomer having at least one acid function is:
   a monocarboxylic acid,
   a dicarboxylic acid,
   an acid anhydride,
   a monoester of said dicarboxylic acid,
   a monoester of said acid anhydride,
   a monoamide of said dicarboxylic acid,
   a monoamide of said acid anhydride, or
   an itaconic acid.

10. The composition according to claim 8, wherein said monomers having at least one sulphonic acid function are vinylsulphonic acid, styrenesulphonic acid or 2-acrylamido-2-methylpropanesulphonic acid.

11. The composition according to claim 1, wherein said plasticizing oligomer is a polymer of at least one monomer, said monomer having an amine function in free form or partially or totally neutralized or alternatively partially or totally quaternized.

12. The composition according to claim 1, wherein said plasticizing oligomer is a polymer of at least one monomer, said monomer is a carboxybetaine or a sulphobetaine obtained by partial or total quaternization of monomers having ethylenic unsaturation and having an amine function with sodium salts of a carboxylic acid having a labile halide or with cyclic sultones.

13. The composition according to claim 1, wherein said plasticizing oligomer is a polymer of at least one monomer wherein said monomer is:
   a hydroxy $(C_1-C_{30})$ alkyl (meth)acrylate;
   a (meth)acrylamide; a di$(C_1-C_{30})$alkyl (meth)acrylamide;
   a N-vinylpyrrolidone; a vinylcaprolactam; or
   a (meth)acrylate of ethylene glycol, of diethylene glycol or of polyethylene glycol having a hydroxyl or ether end.

14. The composition according to claim 1, wherein said plasticizing oligomer is a polyester, polyester/amide, polyamide, polyurethane, polyurea or a mixture thereof, and wherein said plasticizing oligomer is anionic, cationic, amphoteric or nonionic.

15. The composition according to claim 14, wherein said polyester is a:
(i) compound of formula (I):

$$HOOC-(CH_2)_m-COOH \quad (I)$$

wherein m is an integer ranging from 2 to 20;
(ii) compound of formula (II):

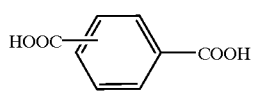

(II)

wherein the labile acid group is in the ortho, para or meta position and wherein it is possible for the benzene ring to contain substituents other than sulphonate groups; or
(iii) mixture of a compound of formula (I) and a compound of formula (II) with a diol said diol is:
(a) a compound of formula (III):

$$HO-(CH_2)_x-OH \quad (III)$$

wherein x is an integer ranging from 2 to 20;
(b) a compound of formula (IV):

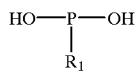

(IV)

wherein P is an aromatic, cycloaliphatic, linear or branched aliphatic trivalent hydrocarbon radical, and $R_1$ denotes a $C_2-C_{30}$ hydrocarbon side chain;

(c) a compound of formula (V):

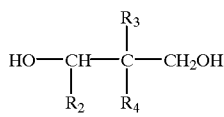

(V)

wherein $R_2$ denotes a hydrogen atom or a linear or branched $C_1$–$C_3$ alkyl radical; $R_3$ denotes a hydrogen atom or a linear or branched $C_1$–$C_4$ alkyl radical and $R_4$ denotes a linear or branched $C_1$–$C_4$ alkyl radical;

(d) a compound of formula (VI):

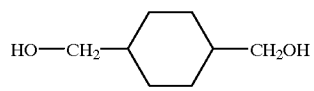

(VI)

(e) a compound of formula (VII):

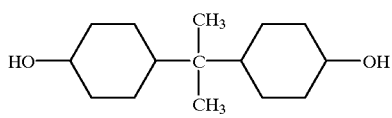

(VII)

or (f) a mixture thereof.

16. The composition according to claim 15, wherein P is a group —$(CH_2)_p$—CH— wherein $p \geq 1$.

17. The composition according to claim 16, wherein P is the group —$(CH_2)$—CH—.

18. The composition according to claim 1, which further comprises a cosmetically or dermatologically acceptable vehicle.

19. The composition according to claim 18, wherein said at least one film-forming polymer and said at least one plasticizing oligomer are dissolved or dispersed in said vehicle, and further wherein said composition is free of nitrocellulose.

20. The composition according to claim 1, wherein said plasticizing oligomer is present in a solids concentration ranging from 0.1 to 80% by weight, relative to the total weight of the composition.

21. The composition according to claim 20, wherein said plasticizing oligomer is present in a solids concentration ranging from 5 to 40% by weight, relative to the total weight of the composition.

22. The composition according to claim 21, wherein said plasticizing oligomer is present in a solids concentration ranging from 10 to 30% by weight, relative to the total weight of the composition.

23. The composition according to claim 1, wherein said film-forming polymer is:

a vinyl acetate/crotonic acid/vinyl tert-butylbenzoate copolymer;

an acrylic acid/ethyl acrylate/N-tert-butylacrylamide copolymer;

an N-octylacrylamide/methyl methacrylate/hydroxypropyl methacrylate/acrylic acid/tert-butylaminoethyl methacrylate copolymer; or an acrylic acid/ethyl acrylate/tert-butyl acrylate terpolymer.

24. The composition according to claim 1, wherein said film-forming polymer is present in said composition at a concentration ranging from 0.1 to 50% by weight, relative to the total weight of the composition.

25. The composition according to claim 24, wherein said film-forming polymer is present in said composition at a concentration ranging from 1 to 30% by weight, relative to the total weight of the composition.

26. The composition according to claim 18, wherein said cosmetically or dermatologically acceptable vehicle is:

water;

one or more organic solvents;

a mixture of water and one or more organic solvents; or a fatty substance selected from the group consisting of mineral oils, plant oils, animal oils, synthetic oils, animal waxes, fossil waxes, plant waxes, mineral waxes and synthetic waxes.

27. The composition according to claim 26, wherein said organic solvents are $C_1$–$C_4$ lower alcohols or a mixture of butyl acetate and ethyl acetate.

28. The composition according to claim 1, wherein said composition further comprises one or more additives selected from the group consisting of thickeners, softeners, antifoaming agents, hydrating agents, wetting agents, treating agents, antiperspirants, basifying agents, acidifying agents, UVA or UVB broad-band sunscreens, dyes, pigments, fragrances, preserving agents, anionic polymers, nonionic polymers, amphoteric polymers and propellants.

29. The composition according to claim 1, wherein said composition is a hair composition.

30. The composition according to claim 1, wherein said composition is a make-up composition.

31. The composition according to claim 1, wherein said composition is a skin care composition.

32. The composition according to claim 1, wherein said composition is a nail varnish composition.

33. A method for treating at least one keratin substance, said method comprising applying to said at least one keratin substance the composition according to claim 1.

34. The method according to claim 33, wherein said at least one keratin substance is the nails, the skin, the hair, the scalp, the eyelashes, the eyebrows or the lips.

* * * * *